United States Patent [19]

Graves et al.

[11] 4,071,617
[45] Jan. 31, 1978

[54] AQUEOUS FLOWABLE CONCENTRATES OF PARTICULATE WATER-INSOLUBLE PESTICIDES

[75] Inventors: Thomas M. Graves, Richmond; Theodore H. Koundakjian, Albany, both of Calif.

[73] Assignee: Chevron Research Company, San Francisco, Calif.

[21] Appl. No.: 656,231

[22] Filed: Feb. 9, 1976

Related U.S. Application Data

[63] Continuation of Ser. No. 206,516, Dec. 9, 1971, abandoned, which is a continuation of Ser. No. 829,769, June 2, 1969, abandoned.

[51] Int. Cl.$^2$ ............... A61K 31/765; A61K 31/40; A61K 31/39; A01N 9/00
[52] U.S. Cl. ................... 424/78; 424/274; 424/276; 71/65; 71/79; 71/DIG. 1
[58] Field of Search .............. 71/DIG. 1; 424/78

[56] References Cited

U.S. PATENT DOCUMENTS 3,060,084  10/1962  Littler ........................ 71/DIG. 1
3,360,356  12/1967  Vartiak ........................ 71/65

Primary Examiner—Lewis Gotts
Assistant Examiner—Catherine L. Mills
Attorney, Agent, or Firm—Dix A. Newell; John Stoner, Jr.; Raymond Owyang

[57] ABSTRACT

Flowable aqueous pesticidal concentrates comprising water, 10 to 80% by weight, based on the water, of a water-insoluble solid particulate pesticide and a vinyl alcohol/vinyl acetate polymer having about 5 to 15 mols of vinyl acetate per 100 mols of copolymer and a molecular weight of at least 50,000, wherein the weight ratio of pesticide to copolymer is in the range of 1:1 and 1000:1. These concentrates are compatible with other agricultural chemicals systems.

11 Claims, No Drawings

AQUEOUS FLOWABLE CONCENTRATES OF PARTICULATE WATER-INSOLUBLE PESTICIDES

This application is a continuation of application Ser. No. 206,516, filed Dec. 9, 1971 now abandoned, which in turn is a continuation of application Ser. No. 829,769, filed June 2, 1969, now abandoned.

FIELD OF THE INVENTION

This invention is concerned with aqueous concentrated compositions of solid, particulate water insoluble pesticide which flow as viscous liquids. It is especially concerned with such a composition that is compatible with other aqueous pesticide systems.

BACKGROUND OF INVENTION

Solid pesticides intended for field dilution with liquids are usually sold in the form of emulsive concentrates, wettable powders, or flowable concentrates. Emulsive concentrates are solutions of a solid pesticide in an appropriate solvent. Usually such solvents are mineral oils, other hydrocarbons and chlorinated hydrocarbons. A surface active compound is also included in such concentrates. When the concentrate is diluted with water or other diluent by the user prior to field application, the surface active compound stabilizes the resulting emulsion.

Wettable powders consist of a pesticide mixed with various amounts of solid fillers such as clay, talc, etc. These powders also include a surface active material to improve their wetting properties. The end-user obtains the wettable powder in the form of a solid mixture. Water is added to this solid mixture in the field to form a suspension of solid pesticide in water suitable for application to crops.

The emulsive concentrate system is not always practical in that many solid pesticides are not soluble in common low-cost solvents. Wettable powders are objectionable in that the user frequently is subjected to contact with the concentrated powder as he dumps it from a container into a mixing apparatus. It is also difficult to measure the solid, wettable powders with the usual liquid measuring devices available to the average user.

Water-insoluble, solid pesticides are most conveniently handled as aqueous flowables. Flowables are concentrated suspensions of a solid pesticide in an aqueous system. In general, there will usually be in excess of 10%, sometimes even as high as 80%, solids in these systems. A flowable has the characteristics of a rather thick liquid; that is, it may be poured from a container and pumped and otherwise handled as a viscous liquid. The purchaser of a flowable merely has to open the container and pour the contents into his mixing tank. After diluting the flowable to the proper concentration with water, it is ready to apply. With an aqueous flowable there is no dust and no hydrocarbon solvent.

However, one significant problem arises with flowables. Many flowable users attempt to apply a flowable along with other pesticides, fertilizers and other soil additives simultaneously from the same apparatus. This apparatus is commonly a sprayer which consists of a mixing and holding tank and a nozzle or other orifice system for spraying the pesticide on intended organisms. The user often attempts to charge all these different materials to the mixing tank along with the necessary water. In most cases, a flowable concentrate will, when treated in such a way, convert to a "cottage-cheese"-type of solid floc which soon plugs the orifices or the spray nozzles. This flocculation occurs because the flowable suspension is "broken" by the presence of the other materials added to the mixing tank.

INVENTION DESCRIPTION

A novel, flowable concentrate has now been discovered which is physically stable under the mixing conditions described above. This flowable concentrate comprises (1) a solid, particulate water-insoluble pesticide, (2) a copolymer of vinyl acetate and vinyl alcohol, and (3) water. More specifically, this flowable concentrate is an aqueous suspension containing from 10 to 80% by weight based on the total, of a solid, particulate water insoluble pesticide having a particle size less than 20 microns and a vinyl alcohol/vinyl acetate copolymer having about 5 to 15 mols of vinyl acetate per 100 mols of copolymer and a molecular weight greater than about 50,000 wherein the weight ratio of said pesticide to said copolymer is in the range of 1:1 to 1000:1.

The pesticide compositions of the present invention are concentrated systems. That is, there is usually as much solid pesticide present as can be incorporated and still give a flowable. In general, based on the total weight of the composition there will be from 10 to 80% by weight of solids. Preferably the solids will constitute about 40 to 60% of the composition.

The amount of vinyl alcohol/vinyl acetate copolymer to be used is based on the quantity of solid pesticide present. It has been found that satisfactory concentrated flowables can be made when the weight ratio of pesticide to polymer is in the range of 1:1 to 1000:1. Preferably a minimum amount of copolymer, consistent with stable, concentrated flowables will be used. In most cases the pesticide:copolymer ratio will be in the range of 10:1 to 100:1.

The copolymers used to form these stable, flowable concentrates are copolymers of vinyl alcohol and vinyl acetate. These copolymers are conveniently prepared by partially hydrolyzing polyvinyl acetate. Depending upon the degree of hydrolysis, the nature of the polymer gradually changes from that of polyvinyl acetate to that of polyvinyl alcohol. For the present use, it has been found that the copolymers must have a molecular weight of at least about 50,000. In terms of viscosity, satisfactory copolymers are those which have a viscosity of 30 to 60 centipoises as measured in a 5% aqueous solution using a Brookfield viscometer with a number 1 spindle at 30 RPM at 20° C. At the same time, satisfactory copolymers must have between about 5 and 15 mols of vinyl acetate per 100 mols of total copolymer, preferably from 11 to 13 mols.

The pesticides that may be used in these stable concentrated flowables must be solids having essentially no significant water solubility (i.e., less than about 0.1 g./100 cc. $H_2O$ at ambient temperature) and a particle size less than 20 $\mu$, usually in the range of 0.5 to 20 $\mu$. Preferably such particles will range in size from 0.5 $\mu$ to 10 $\mu$.

Pesticides, e.g., insecticides, fungicides, viricides, acaricides, herbicides, bactericides, and the like, having the above specifications may be used in the concentrates of this invention. Such solid, water insoluble pesticides are listed as such in *Guide to Chemicals Used in Crop Protection*, Canada Department of Agriculture, 1968. Representative examples of presently available pesticides which may be used in this invention are:

Chlorinated Hydrocarbons: aldrin (1,2,3,4,10,10-hexachloro-1,4,4a,5,8,8a-hexahydro-1,4-endoexo-5,8-dimethanonaphthalene), BHC (benzene hexachloride), DDT and dieldrin.

Carbamates: 4-dimethylamino-m-tolyl-N-methylcarbamate, 4-benzothienyl-N-methylcarbamate, 1-naphthyl-N-methylcarbamate, 3,4-dimethylphenyl-N-methylcarbamate, and 2,6-di-tert.butyl-p-tolyl-N-methyl-carbamate.

Thiazoles: 2-amino-4-methyl-5-carboxanilido-thiazole.

Ureas (including Uracils) and Thioureas: 1-(1-naphthyl)-2-thiourea, 5-bromo-3-sec.butyl-6-methyluracil, chloroxuron (3-[-yl)methyl]--dimethylurea), diuron (3-[3,4-dichlorophenyl]-1,1-dimethylurea), monuron (3-[p-chlorophenyl]-1,1-dimethylurea), linuron (3-[3,4-dichlorophenyl]-1-methoxy-1-methylurea), and neburon (3-[3,4-dichlorophenyl]-1-methyl-1-n-butylurea).

Triazines: atratone (2-ethylamino-4-isopropylamino-6-methoxy-s-triazine), atrazine (2-chloro-4-ethylamino-6-isopropylamino-s-triazine), menazon (S-[(4,6-diamino-s-triazine-2-yl) methyl]0,0-dimethylphosphorodithioate), prometone (2-methoxy-4,6-bis(isopropylamino)-s-triazine), and (2-chloro-4,6,-bis[ethylamino]-s-triazine).

Amines: N-butyl-N-$\alpha,\alpha,\alpha$-trifluoro-2,6-dinitro-p-toluidine.

Organo-metallics: ethylmercurichlorendiimide, triphenyl tin hydroxide and paris green.

Inorganics: sulfur and calcium arsenate.

phosphoroamidites and phosphoroamidates: 4-tert.butyl-2-chlorophenyl methyl methylphosphoroamidite and 0-(2,4-dichlorophenyl)-0-methyl isopropylphosphoroamidothioate.

Phosphates and thiophosphates: methyl parathion, 0,0-dimethyl-0-2,5-dichloro-4-iodophenylthiophosphate and 0,0-diethyl-0-3-chloro-4-methyl-1-oxo-2H-1-benzopyran-7-yl-phosphorothioate.

Carboximides: N-(trichloromethylthio)-cis-$\Delta^4$-tetrahydrophthalimide, N-(trichloromethylthio)phthalimide, N-(1,1,2,2-tetrachloroethylthio)-cis-$\Delta^4$-tetrahydrophthalimide.

Sulfonates: ovex (p-chlorophenyl p-chlorobenzene sulfonate).

Alcohols: 4-chloro-3,5-dimethylphenoxyethanol and dinitrocresol.

Chlorinated phenoxy alkanoic acids: 2,4-dichlorophenoxy acetic acid, 4-(2-dichlorophenoxy) butyric acid and 2-(2,4,5-trichlorophenoxy) propionic acid.

Esters: dimethyl tetrachloroterephthalate.

Ethers: 2,4-dichlorophenyl-4-nitrophenylether.

Sulfur oxides: tetradifon(p-chlorophenyl-2,4,5-trichlorophenyl sulfone).

Sulfides: thiram (tetramethylthiuram disulfide).

Metallic dithiocarbamates: ferbam (ferric dimethyldithiocarbamate) and zinc dimethyldithiocarbamate.

In addition to the pesticide, water and copolymer the flowable concentrates of this invention may contain other materials to improve their physical and/or pesticidal properties. Usually a defoaming agent is included in the composition in a quantity of about 0.5 to 2% of the total composition. Silicon-type defoamers are preferred. Thickeners are often very desirable additives for these compositions. Generally they are used at concentrations in the range of 0.1 to 0.5% of the total composition. Xanthate gum is preferred. Finally, wetting agents are sometimes included in the composition. Such wetting agents are preferably of the anionic type and amount to about 0.1–0.5% of the total composition. One such wetting agent is sodium-N-methyl-N-tall oil acid taurate.

EXAMPLES

The following examples are intended to illustrate the invention described herein. They are not intended to limit the invention described herein.

EXAMPLE 1: PREPARATION OF A PREFERRED FLOWABLE

A laboratory "Osterizer" blender was charged with 1134 parts of water, 820 parts of particulate N-1,1,2,2-tetrachloroethylthio-cis-$\Delta^4$-tetrahydrophthalimide having a particle size of 0.5 to 5 microns, 40 parts of an 88% hydrolyzed polyvinyl acetate having a viscosity of 47 cps, and 20 parts of Antifoam C (commercial silicon antifoaming agent). This mixture was stirred for 5 minutes to form a stable suspension. The resulting product was poured from the blender into another container. In was then passed through a 100 mesh screen and through a 325 mesh screen. There was no deposit upon either screen.

EXAMPLE 2: TESTING THE PREFERRED FLOWABLE OF EXAMPLE 1 FOR STABILITY

Portions of the flowable made as in Example 1 were tested for compatability with other pesticide formulations. In this step, 2 parts of the flowable concentrate of Example 1 were mixed with 5 parts of other materials and then diluted with 100 parts of water. The resulting mixture was shaken for 1 minute, allowed to stand for $\frac{1}{2}$ minute, and then shaken again for $\frac{1}{2}$ minute. This final mixture was passed through a 100 mesh and then through a 325 mesh screen. Evaluation was based on the amount of floc on each screen and upon the stability of the emulsion. Any floc on the 100 mesh screen was judged unsatisfactory. The amount of floc on the 325 screen was evaluated to be within one of four categories: no floc, excellent; traces of floc, good; noticeable floc, satisfactory; more than a noticeable amount of floc, unsatisfactory.

Typical commercial formulations of the following agricultural products were all tested with the composition of Example 1 and found to be excellent:
1. DDT, in a 2 lb/gal. emulsive concentrate;
2. 0,0-dimethyl-S-[4-oxo-1,2,3-benzotriazin-3-(4H)yl-methyl] phosphorodithioate, in a 50% wettable powder;
3. 0,0-dimethyl-S-[4-oxo-1,2,3-benzotriazin-3(4H)yl-methyl] phosphorodithioate, in a 2 lb/gal. emulsive concentrate;
4. DDT, in a 75% wettable powder;
5. Parathion, in a 8 lb/gal. flow emulsive concentrate;
6. TDE, in a 50% wettable powder;
7. S-[2-(ethylsulfinyl)ethyl]-0,0-dimethyl phosphothioate, in a 2 lb/gal. emulsive concentrate;
8. 1-naphthyl-N-methylcarbamate, in a 50% wettable powder.
9. 1-chloro-diethylcarbamoyl-1-propen-2-yl dimethylphosphate, in an 8 lb/gal. water soluble concentrate;
10. DDT, in a 50% wettable powder;
11. Parathion, in a 15% wettable powder;
12. Volck ® oil, in a 70 SSU spray oil emulsive concentrate.

The DDT in a 2 lb/gal. emulsive concentrate was shown to be the composition most likely to cause floculation of a flowable upon mixing and dilution. Various flowables were made according to the procedure of Example 1, and were tested with the DDT emulsive concentrate by the procedure of Example 2. The results of these tests are given in Table I.

TABLE I

PESTICIDE FLOWABLES

| Ex. No. | Name | Pesticide Particle Size | Parts | Copolymer %VAc[1] | Vis.[2](cps) | Parts | Water Parts | Other Compounds Name | Parts | Evaluation |
|---|---|---|---|---|---|---|---|---|---|---|
| 1 | Difolatan®[3] | 0.5–5 | 820 | 12 | 47 | 40 | 1134 | Antifoam C | 20 | Excellent |
| 3 | " | 0.5–5 | 820 | 16 | 38 | 40 | 1134 | Antifoam C | 20 | Unsatisfactory |
| 4 | " | 0.5–5 | 820 | 2 | — | 40 | 1134 | Antifoam C | 20 | Unsatisfactory |
| 5 | " | 25–75 | 820 | 12 | 47 | 40 | 1134 | Antifoam C | 20 | Unsatisfactory |
| 6 | Endosultan[4] | 1–10 | 820 | 12 | 47 | 40 | 1134 | Antifoam C | 20 | Excellent |
| 7 | Captan®[5] | 1–10 | 820 | 12 | 47 | 40 | 1134 | Antifoam C | 20 | Excellent |
| 8 | Difolatan® | 0.5–5 | 820 | 12 | 48 | 40 | 1134 | Antifoam C | 20 | Excellent |
| 9 | " | 0.5–5 | 820 | 12 | 52 | 40 | 1134 | Antifoam C | 20 | Good |
| 10 | " | 0.5–5 | 820 | 12 | 38 | 40 | 1134 | Antifoam C | 20 | Good |
| 12 | " | 0.5–5 | 820 | 12 | 32 | 40 | 1134 | Antifoam C | 20 | Satisfactory |
| 13 | " | 0.5–5 | 820 | 12 | 26 | 40 | 1134 | Antifoam C | 20 | Unsatisfactory |
| 14 | " | 0.5–5 | 820 | 12 | 47 | 40 | 1134 | — | — | Excellent[6] |
| 15 | " | 0.5–5 | 410 | 12 | 47 | 20 | 1134 | Antifoam C | 20 | Excellent |
| 16 | " | 0.5–5 | 1640 | 12 | 47 | 80 | 1134 | Antifoam C | 20 | Excellent |
| 17 | " | 0.5–5 | 2460 | 12 | 47 | 120 | 1134 | Antifoam C | 20 | Excellent |
| 18 | " | 0.5–5 | 3280 | 12 | 47 | 160 | 1134 | Antifoam C | 20 | Excellent |
| 19 | " | 0.5–5 | 820 | 12 | 47 | 2 | 1134 | Antifoam C | 20 | Good |
| 20 | " | 0.5–5 | 820 | 12 | 47 | 10 | 1134 | Antifoam C | 20 | Excellent |
| 21 | " | 0.5–5 | 820 | 12 | 47 | 20 | 1134 | Antifoam C | 20 | Excellent |
| 22 | " | 0.5–5 | 820 | 12 | 47 | 100 | 1134 | Antifoam C | 20 | Excellent |
| 23 | " | 0.5–5 | 820 | 12 | 47 | 200 | 1134 | Antifoam C | 20 | Excellent |

[1]%VAc refers to the % of vinyl acetate in the vinyl acetate/vinyl alcohol copolymer.
[2]Viscosity in centipoises measured on a 5% aqueous solution of the copolymer by a Brookfield viscometer using a number 1 spindle at 30 RPM at 20° C.
[3]N-(1,1,2,2-tetrachloroethylthio)-cis-$\Delta^4$-tetrahydrophthalimide.
[4]6,7,8,9,10-hexachloro-1,5,5a,6,9,9a-hexahydro-6,9-methono-2,4,3-benzodioxathiepin 3-oxide.
[5]N-(trichloromethylthio)-cis$\Delta^4$-tetrahydrophthalamide.
[6]No floc on either screen but a lot of foam.

Example 1 is a highly satisfactory flowable and is one of the preferred flowables of this invention. Examples 3 and 4 compared with Example 1 show that the vinyl acetate portion of the copolymer molecule must be greater than 2% and less than 16%. Example 5 shows that the pesticide particle size must be less than 20 microns. Examples 6 and 7 are flowables made from other pesticides.

Examples 8 through 13 show the effect of changing the molecular weight of the copolymer as measured by the viscosity of aqueous solutions. These examples indicate that a 5% aqueous solution of the polymer should have a viscosity within the range of 30 to 60, preferably 40 to 55 and most preferably about 45 to 50.

Example 14 shows that excellent flowable is produced without an antifoaming agent, but that upon mixing much foam is formed. This formulation should be used, and an external antifoaming agent added if desired. It is peferred to have an antifoaming agent in the composition.

Examples 15 through 19 are satisfactory flowables having different concentrations of solid pesticide. In these examples, solid concentrations range from 25 to 72% respectively.

Exampls 19 through 23 illustrate satisfactory flowables having various pesticide:polymer ratios. In these examples, the ratios range from 400:1 to 4:1 respectively.

Portions of the satisfactory flowable concentrates were stored for 12 months at both room and elevated temperatures, and then evaluated as before. The compositions of this invention were all found to have satisfactory storage stability.

As indicated above, the flowable concentrates of this invention, either by themselves or with other agricultural chemicals, will be further diluted with water to a concentration suitable for application to the plants or other organisms for which they are intended.

What is claimed is:

1. A flowable, viscous, aqueous pesticidal concentrate which is compatible with other pesticides on dilution with water consisting essentially of water, 10 to 80% by weight based on the water, of a solid water-insoluble particulate pesticide having a particle size less than 20 microns and a vinyl alcohol/vinyl acetate polymer having about 5 to 15 mols of vinyl acetate per 100 mols of copolymer and a viscosity of 30 to 60 centipoises as measured in a 5% aqueous solution using a Brookfield viscometer with a number 1 spindle at 30 rpm at 20° C, the weight ratio of pesticide to copolymer being in the range of 1:1 and 1000:1.

2. The pesticidal concentrate of claim 1 wherein the copolymer has a viscosity of 40 to 55 centipoises as measured in a 5% aqueous solution using a Brookfield viscometer with a number 1 spindle at 30 RPM at 20° C.

3. The pesticidal concentrate of claim 1 wherein the pesticide particle size is in the range of 0.5 to 20 microns and the weight ratio of pesticide to copolymer is in the range of 10:1 and 100:1.

4. The pesticidal concentrate of claim 1 wherein the weight percentage of pesticide in the concentrate, based on the water, is in the range of 40 to 60%.

5. The pesticidal concentrate of claim 1 wherein the weight percentage of pesticide in the concentrate, based on the water, is in the range of 40 to 60%, the particle size of the pesticide is in the range of 0.5 to 10 microns, the copolymer has 11 to 13 mols of vinyl acetate per 100 mols of copolymer and a viscosity of 30 to 60 centipoises as measured in a 5% aqueous solution using a Brookfield viscometer with a number 1 spindle at 30 RPM at 20° C. and the weight ratio of pesticide to copolymer is in the range of 10:1 to 100:1.

6. The pesticide concentrate of claim 1 wherein the weight percentage of pesticide in the concentrate, based on the water, is in the range of 40 to 60%, the particle size of the pesticide is in the range of 0.5 to 10 microns, the copolymer has a viscosity of 40 to 55 centipoises as measured in a 5% aqueous solution using a Brookfield viscometer with a number 1 spindle at 30 rpm at 20° C and the weight ratio of pesticide to copolymer is in the range of 10:1 and 100:1.

7. The pesticidal concentrate of claim 6 wherein the pesticide is N-(1,1,2,2-tetrachloroethylthio-cis-$\Delta^4$-tetrahydrophthalimide, 6,7,8,9,10,10-hexachloro-1,5,5a,6,9,9a-hexahydro-6,9-methono-2,4,3-benzodioxathiepin 3-oxide, or N-(trichloromethylthio)-cis-$\Delta^4$-tetrahydrophthalimide.

8. The pesticidal concentrate of claim 6 wherein the concentrate additionally contains, based on total composition, about 0.5 to 2% of a defoaming agent and about 0:1 to 0.5% of a thickener.

9. The pesticidal concentrate of claim 1 wherein the concentrate additionally contains about 0.5 to 2%, based on total composition, of a defoaming agent.

10. The pesticidal concentrate of claim 1 wherein the concentrate additionally contains about 0.1 to 0.5%, based on total composition, of a thickener.

11. The pesticidal concentrate of claim 1 wherein the concentrate additionally contains about 0.1 to 0.5%, based on total composition, of a wetting agent.

* * * * *